(12) United States Patent
Michler et al.

(10) Patent No.: US 7,794,474 B2
(45) Date of Patent: Sep. 14, 2010

(54) ENDOVASCULAR FLEXIBLE STAPLING DEVICE

(75) Inventors: Robert E. Michler, Columbus, OH (US); Shunichi Homma, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 654 days.

(21) Appl. No.: 10/104,876

(22) Filed: Mar. 21, 2002

(65) Prior Publication Data

US 2002/0099389 A1   Jul. 25, 2002

Related U.S. Application Data

(63) Continuation of application No. 09/242,969, filed as application No. PCT/US97/14772 on Aug. 22, 1997, now Pat. No. 6,482,224.

(60) Provisional application No. 60/024,640, filed on Aug. 22, 1996.

(51) Int. Cl.
*A61B 17/10* (2006.01)
*A61B 17/08* (2006.01)

(52) U.S. Cl. ............... 606/219; 606/139; 227/175.1

(58) Field of Classification Search ........... 606/219, 606/143, 139, 142; 227/175.1, 175.3
See application file for complete search history.

(56) References Cited

U.S. PATENT DOCUMENTS

| | | | |
|---|---|---|---|
| 2,275,167 A | 3/1942 | Bierman | |
| 2,888,928 A | 6/1959 | Seiger | |
| 3,490,442 A | 1/1970 | Streu | |
| 3,906,955 A | 9/1975 | Roberts | |
| 4,307,720 A | 12/1981 | Weber, Jr. | |
| 4,326,529 A | 4/1982 | Doss et al. | |
| 4,473,077 A | 9/1984 | Noiles et al. | |
| 4,485,817 A | 12/1984 | Swiggett | |
| 4,562,838 A | 1/1986 | Walker | |
| 4,682,596 A | 7/1987 | Bales et al. | |
| 4,884,567 A | 12/1989 | Elliott et al. | |
| 4,911,159 A | 3/1990 | Johnson et al. | |
| 4,919,129 A | 4/1990 | Weber, Jr. et al. | |
| 4,976,711 A | 12/1990 | Parins et al. | |

(Continued)

FOREIGN PATENT DOCUMENTS

EP    135840 A2    4/1985

(Continued)

OTHER PUBLICATIONS

Anzola et al., "Potential Source of Cerebral Embolism in Migraine with Aura," *Neurology* (1999) 52(8): 1622.

(Continued)

*Primary Examiner*—Darwin P Erezo
*Assistant Examiner*—Melissa Ryckman
(74) *Attorney, Agent, or Firm*—William H. Dippert; Eckert Seamans Cherin & Mellott, LLC

(57) ABSTRACT

The present invention concerns a flexible stapling device (1). More particularly, this invention concerns a flexible endovascular stapling device (1) for an intravascular procedure such as patent foramen ovale closure, which is designed to avoid open heart surgery by permitting the closure of the defect utilizing a stapling means (26) which is positioned by using a flexible shaft/guidewire system.

20 Claims, 2 Drawing Sheets

U.S. PATENT DOCUMENTS

| | | | |
|---|---|---|---|
| 4,986,889 A | 1/1991 | Charamathieu et al. |
| 5,042,707 A | 8/1991 | Taheri |
| 5,055,100 A | 10/1991 | Olsen |
| 5,057,107 A | 10/1991 | Parins et al. |
| 5,071,418 A | 12/1991 | Rosenbaum |
| 5,078,717 A | 1/1992 | Parins et al. |
| 5,099,827 A | 3/1992 | Melzer et al. |
| RE33,925 E | 5/1992 | Bales et al. |
| 5,125,928 A | 6/1992 | Parins et al. |
| 5,156,608 A | 10/1992 | Troidl et al. |
| 5,171,311 A | 12/1992 | Rydell |
| 5,195,959 A | 3/1993 | Smith |
| 5,196,007 A | 3/1993 | Ellman et al. |
| 5,197,963 A | 3/1993 | Parins |
| 5,209,756 A | 5/1993 | Seedhom et al. |
| 5,295,955 A | 3/1994 | Rosen et al. |
| 5,336,252 A | 8/1994 | Cohen |
| 5,342,413 A | 8/1994 | Hirschberg et al. |
| 5,345,935 A | 9/1994 | Hirsch |
| 5,370,675 A | 12/1994 | Edwards et al. |
| 5,423,834 A * | 6/1995 | Ahmed ............... 606/140 |
| 5,500,012 A | 3/1996 | Brucker et al. |
| 5,505,730 A | 4/1996 | Edwards |
| 5,507,744 A | 4/1996 | Tay et al. |
| 5,665,109 A | 9/1997 | Yoon |
| 5,709,224 A | 1/1998 | Behl et al. |
| 5,730,742 A | 3/1998 | Wojciechowicz |
| 5,782,899 A | 7/1998 | Imran |
| 5,814,065 A | 9/1998 | Diaz |
| 5,846,196 A | 12/1998 | Siekmeyer et al. |
| 5,855,312 A | 1/1999 | Toledano |
| 5,871,443 A | 2/1999 | Edwards et al. |
| 5,919,200 A | 7/1999 | Stambaugh et al. |
| 5,944,738 A | 8/1999 | Amplatz et al. |
| 5,972,023 A | 10/1999 | Tanner et al. |
| 5,972,024 A | 10/1999 | Northrup, III et al. |
| 6,004,316 A | 12/1999 | Laufer |
| 6,036,699 A | 3/2000 | Andreas et al. |
| 6,056,760 A | 5/2000 | Kishigami et al. |
| 6,149,660 A * | 11/2000 | Laufer et al. ............... 606/143 |
| 6,156,032 A | 12/2000 | Lennox |
| 6,290,674 B1 | 9/2001 | Roue et al. |
| 6,325,798 B1 | 12/2001 | Edwards et al. |
| 6,401,720 B1 | 6/2002 | Gifford et al. |
| 6,419,669 B1 | 7/2002 | Frazier et al. |
| 6,436,088 B2 | 8/2002 | Frazier et al. |
| 6,456,865 B2 | 9/2002 | Samson |
| 6,458,100 B2 | 10/2002 | Roue et al. |
| 6,482,224 B1 | 11/2002 | Homma et al. |
| 6,514,250 B1 | 2/2003 | Jahns et al. |
| 6,558,314 B1 | 5/2003 | Adelman et al. |
| 6,584,360 B2 | 6/2003 | Francischelli et al. |
| 6,589,237 B2 | 7/2003 | Woloszko |
| 6,606,523 B1 | 8/2003 | Jenkins |
| 6,641,604 B1 | 11/2003 | Adelman |
| 6,645,202 B1 | 11/2003 | Pless et al. |
| 6,645,225 B1 | 11/2003 | Atkinson |
| 6,648,897 B2 | 11/2003 | Hamilton |
| 6,652,518 B2 | 11/2003 | Wellman et al. |
| 6,669,693 B2 | 12/2003 | Friedman |
| 6,682,546 B2 | 1/2004 | Amplatz |
| 6,702,835 B2 | 3/2004 | Ginn |
| 6,712,804 B2 | 3/2004 | Roue et al. |
| 6,712,836 B1 | 3/2004 | Berg et al. |
| 6,716,211 B2 | 4/2004 | Mulier et al. |
| 6,730,108 B2 | 5/2004 | Van Tassel et al. |
| 6,736,810 B2 | 5/2004 | Hoey et al. |
| 6,755,790 B2 | 6/2004 | Stewart et al. |
| 6,790,218 B2 | 9/2004 | Jayaraman |
| 6,846,319 B2 | 1/2005 | Ginn et al. |
| 6,887,238 B2 | 5/2005 | Jahns et al. |
| 2001/0037129 A1 | 11/2001 | Thill |
| 2002/0143322 A1 | 10/2002 | Haghighi |
| 2003/0028189 A1 | 2/2003 | Woloszko et al. |
| 2003/0045893 A1 | 3/2003 | Ginn |
| 2003/0050665 A1 | 3/2003 | Ginn |
| 2003/0065364 A1 | 4/2003 | Wellman et al. |
| 2003/0069570 A1 | 4/2003 | Witzel |
| 2003/0120268 A1 | 6/2003 | Bertolero et al. |
| 2003/0144694 A1 | 7/2003 | Chanduszko et al. |
| 2003/0225421 A1 | 12/2003 | Peavey et al. |
| 2003/0233091 A1 | 12/2003 | Whayne et al. |
| 2004/0098031 A1 | 5/2004 | Van der Burg et al. |
| 2004/0098042 A1 | 5/2004 | Devellian et al. |
| 2004/0102721 A1 | 5/2004 | McKinley |
| 2004/0143292 A1 | 7/2004 | Marino et al. |
| 2004/0153057 A1 | 8/2004 | Davison |
| 2004/0153098 A1 | 8/2004 | Chin et al. |
| 2004/0176799 A1 | 9/2004 | Chanduszko et al. |
| 2004/0220596 A1 | 11/2004 | Frazier et al. |
| 2004/0249398 A1 | 12/2004 | Ginn |
| 2005/0021059 A1 | 1/2005 | Cole et al. |
| 2005/0033288 A1 | 2/2005 | Auth et al. |
| 2005/0033327 A1 | 2/2005 | Gainor et al. |
| 2005/0055050 A1 | 3/2005 | Alfaro |
| 2005/0065506 A1 | 3/2005 | Phan |
| 2005/0065509 A1 | 3/2005 | Coldwell et al. |
| 2005/0070923 A1 | 3/2005 | McIntosh |
| 2005/0119675 A1 | 6/2005 | Adams et al. |

FOREIGN PATENT DOCUMENTS

| | | |
|---|---|---|
| EP | 199694 A2 | 10/1986 |
| EP | 265532 A1 | 5/1988 |
| EP | 375556 A1 | 6/1990 |
| EP | 428812 A1 | 5/1991 |
| EP | 947165 A1 | 10/1999 |
| GB | 1260919 | 1/1972 |
| GB | 1550676 | 8/1979 |
| GB | 2 359 024 A | 8/2001 |
| WO | WO 85/00018 A1 | 1/1985 |
| WO | WO 90/04352 A1 | 5/1990 |
| WO | WO 91/15996 A1 | 10/1991 |
| WO | WO 92/04864 A1 | 4/1992 |
| WO | WO 93/05705 A1 | 4/1993 |
| WO | WO 93/15791 A1 | 8/1993 |
| WO | WO 94/00178 A1 | 1/1994 |
| WO | WO 98/07375 | 2/1998 |
| WO | WO 99/18862 A1 | 4/1999 |
| WO | WO 99/18864 A1 | 4/1999 |
| WO | WO 00/07506 A2 | 2/2000 |
| WO | WO 00/09027 A1 | 2/2000 |
| WO | WO 01/78596 A1 | 10/2001 |
| WO | WO 03/022159 A1 | 3/2003 |
| WO | WO 03/022160 A1 | 3/2003 |
| WO | WO 03/026496 A2 | 4/2003 |
| WO | WO 03/053493 | 7/2003 |
| WO | WO 03/071957 A2 | 9/2003 |
| WO | WO 03/082076 | 10/2003 |
| WO | WO 03/094742 A1 | 11/2003 |
| WO | WO 2004/019791 A2 | 3/2004 |
| WO | WO 2004/082532 A1 | 9/2004 |
| WO | WO 2004/091411 A2 | 10/2004 |
| WO | WO 2005/006990 A2 | 1/2005 |
| WO | WO 2005/027753 A1 | 3/2005 |
| WO | WO 2005/034738 A2 | 4/2005 |

OTHER PUBLICATIONS

De Castro et al., "Morphological and Functional Characteristics of Patent Foramen Ovale and Their Embolic Implications," *Stroke* (Oct. 2002), pp. 2407-2413.

Cordis Corporation, Cordis Ducor® Lumeleo™ Electrode Catheters [brochure], Cordis Corporation, (Dec. 1984), 2 pages.

Del Sette, "Migraine with Aura and Right-to-Left Shunt on Transcranial Doppler: A Case Control Study," *Cerebrovas Dis* (1998) 8:327-330.

Gillette, "Catheter Ablation in Dysrhythmias," *Cardio*, (Mar. 1984), pp. 67-69.

Ho et al., "Morphological Features Pertinent to Interventional Closure of Patent Oval Foramen," *J Interventional Cardiology*, vol. 16 No. 1, (2003), pp. 33-34.

Kennedy et al., "High-burst-Strength, feedback-controlled bipolar vessel sealing," *Surg Endosc* (1998) 12:876-878.

Koenig et al., "Role of Intracardiac Echocardiographic Guidance in Transcatheter Closure of Atrial Septal Defects and Patent Foramen Ovale Using the Amplatzer® Device," *J. Interventional Cardiology*, (2003) 16 (1): 51-62.

Morady, "Transvenous Catheter Ablation of a Posterospetial Accessory Pathway in a Patient with the Wolff Parkinson-White Syndrome," *The New England Journal of Medicine*, (Mar. 15, 1984), 310(11): 705-707.

Morandi et al., "Transcatheter Closure of Patent Foramen Ovale: A New Migraine Treatment?" *J Interventional Cardiology*, (2003), 16(1): 39-42.

Pfleger, "Haemodynamic Quantification of Different Provocation Manoeuvres by Simultaneous Measurement of Right and Left Atrial Pressure: Implications for the Echocardiographic Detection of Persistent Foramen Ovale," *Eur J Echocardiography* (2001) 2: 88-93.

Polgar et al., "A New Technique for Closed-Chest Human His Bundle Ablation Using Suction Electrode Catheter and DC Shock," In: Perez Gomez F, ed. *Cardiac Pacing Electrophysiology Tachyarrhythmias*. Madrid, Spain: Grouz Publishers; 1985:1582-1586.

Polgar et al., "Comparison of Two Different Techniques for Closed-Chest His Bundle Ablation," In: Perez Gomez F, ed. Cardiac Pacing Electrophysiology Tachyarrhythmias. Madrid, Spain: Grouz Publishers; 1985:1578-1587.

Polgar, "Closed Chested Ablation of His Bundle: A New Technique Using Suction Electorde Catheter and DC Shock," *Nachdruck Aus: Cardio Pacing*, (1983), pp. 883-890.

Stuart, "What's All the Flap About PFO Closure?," *Start-Up: Windhover's Review of Emerging Medical Ventures*, (Nov. 10, 2004), pp. 9-14.

Sztajzel et al., "Patent Foramen Ovale, a Possible Cause of Symptomatic Migraine: A Study of 74 Patients with Acute Ischemic Stroke," *Cerebrovas Dis* (2002) 13: 102-106.

Thomas, "Patent Foramen Ovale with Right-to-left Shunting: Echocariographic Alternatives," *Eur J Echocariography* (2001) 2:74-75.

Wilmhurst et al., "Effect on Migraine of Closure of Cardiac Right-to-Left Shunts to Prevent Recurrence of Decompression Illness of Illness or Stroke or for Haemodynamic Reasons," *The Lancet*, vol. 356, (Nov. 11, 2000), pp. 1648-1651.

Wilmhurst et al., "Relationship between Migraine and Cardiac and Pulmonary Right to Left Shunts," *Clinical Science* (2001) 100:215-220.

\* cited by examiner

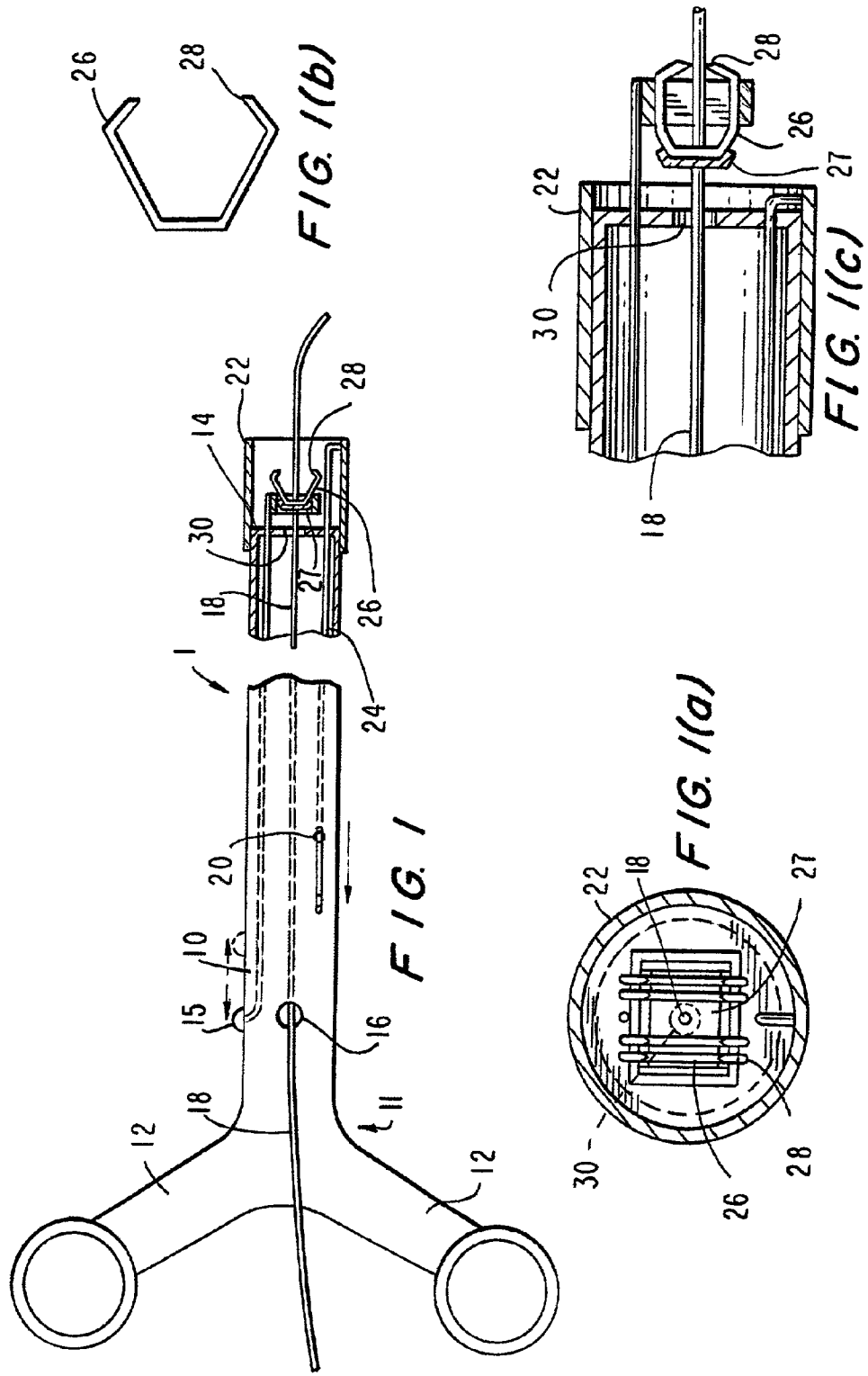

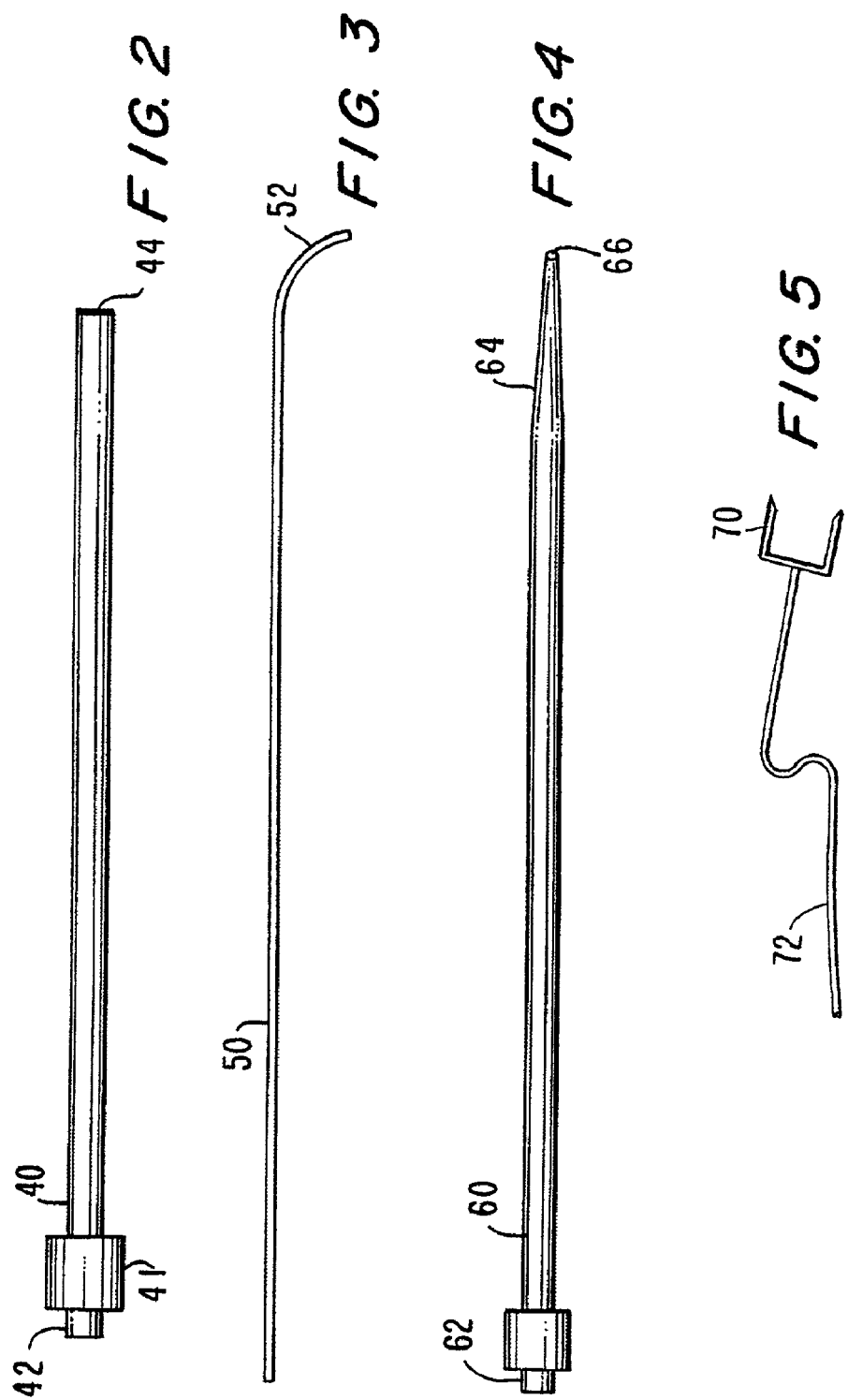

ENDOVASCULAR FLEXIBLE STAPLING DEVICE

CROSS-REFERENCE TO RELATED APPLICATION

This application is a continuation of commonly assigned, U.S. patent application Ser. No. 09/242,969, filed Jun. 7, 1999, now U.S. Pat. No. 6,482,224 which in turn is a National Phase application of PCT Patent Application No. PCT/US97/14772, filed Aug. 22, 1997, which in turn is based upon commonly assigned, co-pending U.S. Provisional Patent Application Ser. No. 60/024,640 filed Aug. 22, 1996.

FIELD OF THE INVENTION

The present invention relates to a flexible stapling device. More particularly, this invention relates to a flexible endovascular stapling device useful for intravascular procedures such as patent foramen ovale closure, atrial septal defect closure, valve repair, or valve replacement, which is designed to avoid open heart surgery by permitting the closure of the defect and/or valve repair or replacement utilizing a stapling means which is positioned by using a flexible shaft/guide wire system or by direct vision.

BACKGROUND OF THE INVENTION

Cryptogenic strokes potentially account for 40% of the 500,000 strokes which occur in the United States each year. Many of these events may be associated with a patent foramen ovale (small atrial septal defect) which permits debris in the venous circulation to cross over into the arterial circulation where it may travel to the brain. Treatment for these patients often includes open heart surgery to close the defect.

A number of prior art references are known:

U.S. Pat. No. 4,473,077, which issued to Noiles et al on Sep. 25, 1984, discloses a flexible shafted surgical stapler generally useful for anastomosis procedures;

U.S. Pat. No. 4,485,817, which issued to Swiggett on Dec. 4, 1984, teaches a stapler with flexible shaft construction having hydraulic transmission/drive means. This stapler is used primarily for anastomosis of hollow body vessels; and U.S. Pat. No. 5,042,707, which issued to Taheri on Aug. 27, 1991, relates to an articulated stapler for use in the vascular system.

However, none of the above references teaches the use of a flexible stapler for intravascular procedures such as patent foramen ovale closure or a flexible stapler suitable for these procedures.

OBJECTS OF THE INVENTION

It is an object of the invention to provide an endovascular flexible stapling device.

It is also an object of the invention to provide an endovascular flexible stapling device useful for closure of a patent foramen ovale defect, atrial or ventricular septal defect closure, valve repair, or valve replacement, without the need for open heart surgery.

It is a further object of the invention to provide a method of performing intravascular procedures whereby a endovascular flexible stapling device is inserted into a body.

It is a yet further object of the invention to provide for a method of closing a patent foramen ovale defect, atrial or ventricular septal defect closure, valve repair, or valve replacement, without the need for open heart surgery.

These and other objects of the invention will become apparent from the following discussion of the invention.

SUMMARY OF THE INVENTION

The present invention provides for a endovascular flexible stapling device. More particularly, this invention provides for a flexible endovascular stapling device for a procedure such as patent foramen ovale closure, which is designed to avoid open heart surgery by permitting the closure of the defect utilizing a stapling means which is positioned by using a flexible shaft/guide wire system introduced via the femoral vein or the jugular vein. One application for the flexible stapling device of the present invention is to pass the device via a femoral vein into the right atrium of the heart and, with the guidance of transesophageal echocardiography, position the device, and then fire one or more staples to obtain closure of the defect.

The construction and obvious advantages of the system provided for by the present invention will be more clearly understood from the following description of the various specific embodiments when read in conjunction with the accompanying drawings.

BRIEF DESCRIPTION OF THE DRAWINGS

FIG. 1 is a longitudinal, partly cross-sectional view of the flexible stapling device of the present invention;

FIG. 1(a) is an end view of the flexible stapling device of FIG. 1 showing in cross-section the position of the staples prior to use for effecting closure of a defect;

FIG. 1(b) is a lateral view of a typical staple which is incorporated into the distal end of the device of FIG. 1;

FIG. 1(c) is a cross-sectional view of the distal end of the device of FIG. 1(a), showing a staple in a closed position;

FIG. 2 is a longitudinal view of the introducer element used for insertion of the flexible stapling device;

FIG. 3 is a longitudinal view of the guidewire upon which the flexible stapling device of the present invention glides to position the device in proximity to the defect to be closed;

FIG. 4 is a longitudinal view of a typical dilator which is used for gradually increasing the size of a vein to permit the easy introduction of the flexible stapling device of the present invention; and FIG. 5 is a perspective view of a staple useful according to the invention.

DETAILED DESCRIPTION OF THE INVENTION

The present invention is directed to an endovascular flexible stapling device. More particularly, this invention relates to a transfemoral flexible stapling device useful for a number of intravascular procedures. For example, the flexible stapling device can be used for patent foramen ovale closure which is designed to avoid open heart surgery by permitting the closure of the defect utilizing a stapling means which is positioned by using a flexible shaft/guide wire system. However, the device can also be used for atrial or ventricular septal defect closure or valve repair or replacement by an endovascular route or by direct vision.

As noted above, many of the cryptogenic strokes which occur in the United States each year can be associated with the existence of the small atrial septal defects known as patent foramen ovale defects. Historically the primary treatment used for patients who may have been diagnosed with such defects has been medical therapy with anticoagulants or antiplatelet agents, or open heart surgery to repair the septal defect.

The device of the present invention is designed to avoid open heart surgery by allowing for the closure of the septal defect utilizing a flexible shaft device which incorporates a stapling means. This device may be introduced by a femoral vein into the right atrium of the patient's heart where, with the guidance of transesophageal echocardiography, the device may be positioned and staples may be fired.

The invention can perhaps be better appreciated by making reference to the drawings. With reference to FIG. 1 a longitudinal, partly cross-sectional view of the flexible stapling device 1 of the present invention is shown, wherein the essential components are depicted. A flexible catheter shaft 10 is shown which incorporates at the proximal end 11 multiple hand grips 12 for maneuvering the device 1 into a patient's vein and properly locating the distal end 14 in proximity to the defect to be closed. Distal to the hand grips 12 is a guidewire port 16, through which passes the proximal end of a guidewire 18 over which the flexible stapling device 1 slides and is guided into position. Guidewire port 16 could optionally be located elsewhere, for example, at the proximal portion 17 of hand grips 12.

Distal to guidewire port 16 is a slide mechanism 20 for retracting a retractable external housing 22, located at the distal end 14 of flexible shaft 10. Slide mechanism 20 is operatively connected by suitable actuation means 24 to retractable external housing 22 to facilitate retraction of the housing 22 once the distal end 14 of the device 1 has been properly positioned in proximity to the defect to be closed. Retractable housing 22 could comprise a cylindrical member having an inner diameter slightly greater then the outer diameter of shaft 10.

Located within retractable housing 22 are one or more, preferably 2 or 4, barbed staples 26 which have been properly positioned to present intimate contact between the barbed tips 28 of the staples 26 and the portion of the patient's septum to be closed once external housing 22 has been retracted.

FIG. 1a is a cross-sectional view of the distal end of the flexible device 1 of FIG. 1 showing four separate barbed staples 26 releasably positioned on a staple holding member 27 within external housing 22. Each of the staples 26 has been preformed and has barbed ends 28 for insertion into the septum wall presenting the defect. Holding member 27 for the staples 26 has a guidewire exit port 30 through which the guidewire 18 extends distally from the flexible shaft 10 of the device.

An actuator such as handgrips 12 or, optionally, an actuator 15, is operatively connected to holding member 27 and/or staple closer 25, so that staples 26 are simultaneously closed and released when the handgrips 12 are squeezed together or actuator 15 is activated. The operative connection can be mechanical, electrical, or other. After discharge of staples 26, holding member 27 could be either re-fitted with new staples 26 or replaced with a replacement holding member 27 with staples already in place, e.g., a "clip".

In FIG. 1b a typical barbed staple 26 is depicted showing the angular preformed configuration of the staple 26. The barbed tips 28 allow for the insertion of the staples to effect closure of the defect without allowing them to spontaneously release from the wall in which they have been inserted.

FIG. 1(c) represents the distal end of flexible device 1 where external housing 22 has been retracted and staple 26 has been closed. Barbed ends 28 of staple 26 are in a closed, almost touching position. In one embodiment of the invention, staple closer 25 moves distally relative to holding member 27 to cause barbed ends 28 to close on the intended target tissue or organ, such as the septum. Optionally, other mechanisms that can be activated proximally, are operatively connected to a distal staple holding member, and cause the staples to close on an intended target could be used in place of the system described here. Also, it is contemplated that the device 1 could optionally comprise fiber optics and/or light or imaging transmitting means, as well as one or more working channels or lumens.

With reference to FIG. 2, a longitudinal view of an introducer element 40 of the system of the present invention is depicted. A one way-valve 42 is located at the proximal end 41 of the introducer element 40 and a generally circular opening 44 is located at the distal end thereof.

FIG. 3 depicts a perspective view of the guidewire 50 showing a curved tip 52 at the distal end thereof.

FIG. 4 depicts a perspective view of a typical dilator 60, which can be a set of 2 or more progressively larger dilators for gradual dilation of a vein or artery. The last dilator passes first through introducer 40 and then into, for example, a vein. In a set of three dilators, the lengths could be 20 cm, 20 cm, and 55 cm. An orifice 62 is located at the proximal end of dilator 60 for passage of the guidewire. A tapered tip 64 is located near the distal end thereof, and a generally circular opening 66 is located at the distal end.

It is contemplated that the flexible shaft of the stapling device of the present invention may be effectively constructed of a suitable wire-reinforced polymeric material. Preferably the material chosen should allow for the easy curvature of the shaft of the device without the need for excessive forces being applied, while at the same time providing for the necessary overall rigidity to the shaft to allow for the insertion of the device in the patient's vein.

In overall length the flexible stapling device depicted in FIG. 1 will be approximately 110 cm. Shorter or longer overall lengths, for example, of from about 80 to about 150 cm, are also contemplated as may be required to effect a particular procedure.

The overall diameter of the cross-section of the flexible shaft 10 of the device 1 depicted in FIG. 1 is approximately 5 mm. It is contemplated that similar devices may be constructed having overall diameters of the flexible shaft which vary somewhat to accommodate the different size veins into which the device must be inserted. Therefore, shaft diameters could range from about 5 to about 15 mm.

The retractable external housing 22 at the distal end of the device 1 will have an overall diameter of approximately 5.5 mm to 16 mm. Again, variations in this diameter are contemplated depending upon the needs of a particular procedure and to accommodate patients having unduly small veins.

The barbed staples which are located at the distal end of the stapler device will have an overall length of approximately 4 mm to 14 mm. Again, the precise configuration of the staple, the actual dimensions of the barbs as well as the overall size of the staple itself, are variables which will be determined by the conditions which prevail in carrying out any particular procedure and the physiological requirements of the patient involved.

The number and actual location of staples within the retractable external housing 22 may also vary depending upon the needs of a particular procedure.

In an optional embodiment of the invention shown in FIG. 5, each staple 70 may have a filament 72 extending from staple 70 a sufficient length that the proximal end of each filament would extend outside the patient's body. Then, if staple 70 were not positioned properly, the surgeon could retrieve staple 70 by pulling firmly on filament 72. If staple 70 is properly positioned, filament 72 would merely be cut. It is contemplated that a length of from about 20 to 100 cm of filament 72 would be fixedly attached to each staple 70. The filaments 72 could be comprised of any flexible, physiologically acceptable natural or manufactured material, such as acetates or poly-acetates, etc., used in sutures. The distal end of each filament 72 would be glued or physically affixed to each staple 70.

With regard to the introducer element depicted in FIG. 2 it is generally contemplated that the overall length of this element, taken from the base of the one-way valve located at the proximal end thereof to the distal tip of the element, will be from about 30 to 60 cm, preferably approximately 50 cm. The overall diameter of the introducer element at the distal end will be from about 6 mm to 20 mm, or as initially depicted approximately 6.7 mm, to accommodate the passage of the flexible shaft stapling device through the opening provided.

The guidewire which is depicted in FIG. 3 will have an overall length of at least from about 90 to 130 cm, preferably 110 cm, to properly function with the flexible shaft stapling device depicted in FIG. 1. The overall diameter of the guidewire will generally be from about 0.30 to 0.50 mm, preferably about 0.38 mm, although variations in the actual diameter of the guidewire are contemplated.

The dilator depicted in FIG. 4 is typical of a series of three or more dilators which vary in length from about 20 to 55 cm.

The overall diameter of the largest cross-section of each dilator will be no more than the opening provided at the distal end of the introducer element. It is, therefore, contemplated that the overall diameter of the dilators will be from about 5 to 15 mm.

In the method of the invention one or more of the smaller diameter dilators is inserted into a femoral vein to permit gradual enlargement of the patient's vein using successively larger diameter dilators and ultimately to allow entry of the introducer element. The largest in the series of dilators used will be inserted first through the introducer element and then into the vein which had been previously enlarged using smaller diameter dilators.

After the introducer element has been properly positioned within the patient's vein, and the guidewire positioned through the defect, a flexible stapling device according to the invention is then inserted through the introducer over the guidewire and with the aid of trans-esophageal echocardiography or other similar procedure, the distal end of the flexible stapler device is positioned adjacent or near to the patent foramen ovale requiring closure. The staples are then propelled or fired by retracting the external housing utilizing the slide mechanism provided in the proximal end of the flexible stapler shaft.

While, as described above, the flexible stapling device of the invention is useful for patent foramen ovale closure, there are other intravascular procedures for which the flexible stapling device can be used. Such procedures include, for example, the correction of atrial septal or ventricle septal defect, closure of paravalvular leaks, or annuloplasty repair of valvular insufficiency or valve replacement.

Also, the flexible stapling device need not be inserted percutaneously. In certain applications a cut down procedure at the leg can be employed with direct vision of the procedure or with the heart open during minimally invasive surgery. In addition, multiple sizes of the flexible stapling device should be available.

It will be further apparent to one skilled in this art that the improvements provided for in the present invention, while described with relation to certain specific physical embodiments also lend themselves to being applied in other physical arrangements not specifically provided for herein, which are nonetheless within the spirit and scope of the invention taught here.

We claim:

1. A flexible shaft stapling device comprising:
   a generally elongated flexible shaft having a longitudinal axis, proximal and distal ends, and an exterior surface;
   an actuator located at the proximal end of said flexible shaft;
   a guidewire entry port located at the proximal end of said flexible shaft;
   a guidewire exit port located at the distal end of said flexible shaft;
   a retractable housing having proximal and distal ends and being slidably located at and at least partially surrounding the distal end of the flexible shaft;
   a staple holding member within the retractable housing at the distal end of said flexible shaft, said staple holding member being adapted for releasably holding at least one staple; and
   a stapler closer within the retractable housing and operatively connected to the actuator for closing a staple,
   wherein the retractable housing is capable of being retracted proximally along the longitudinal axis over the exterior surface of the flexible shaft to expose the staple holding member and wherein said staple closer and said staple holding member are operatively connected to the actuator so as to close and release a staple.

2. The flexible shaft stapling device of claim 1, wherein the flexible shaft is constructed of a suitable wire reinforced plastic material.

3. The flexible shaft stapling device of claim 1, further comprising a staple within the retractable housing at the distal end of said flexible shaft.

4. The flexible shaft stapling device of claim 3, wherein the staple is preformed to effect ease of closure upon contact with the wall of a patient's heart or blood vessel.

5. The flexible shaft stapling device of claim 3, wherein 2 or 4 individual staples are provided within the retractable housing.

6. The flexible shaft stapling device of claim 1, wherein the overall length of the flexible stapling device is from about 80 to 150 cm.

7. The flexible shaft stapling device of claim 6, wherein the overall length of the flexible stapling device is approximately 110 cm.

8. The flexible shaft stapling device of claim 1, wherein the overall diameter of the cross-section of the flexible shaft is from about 5 to about 15 mm.

9. The flexible shaft stapling device of claim 8, wherein the overall diameter of the cross-section of the flexible shaft is approximately 5 mm.

10. The flexible shaft stapling device of claim 3, wherein the staple has an overall length of approximately 4 mm to 14 mm.

11. The flexible shaft stapling device of claim 10, wherein the staple is preformed.

12. The flexible shaft stapling device of claim 5, wherein two or more of the staples can be released simultaneously.

13. The flexible shaft stapling device of claim 1, wherein the actuator is operatively connected to said staple holding member so that the staple is released from the staple holding member upon actuation of the actuator.

14. The flexible shaft stapling device of claim 1, wherein the retractable housing has an overall diameter of approximately 55 mm to 16 mm.

15. The device of claim 1, wherein the retractable housing is cylindrical or substantially cylindrical.

16. A system comprising:
   at least one staple; and
   a flexible shaft stapling comprising:
      a generally elongated flexible shaft having a longitudinal axis, proximal and distal ends, and an exterior surface and having a length sized to pass via a femoral vein into the right atrium of the heart;
      an actuator located at the proximal end of the flexible shaft;
      a retractable housing having proximal and distal ends and being slidably located at and at least partially surrounding the distal end of the flexible shaft;
      a staple holding member within the retraceable housing at the distal end of said flexible shaft, said staple holding member being adapted for releasably holding at least one staple; and
      a stapler closer within the retractable housing and operatively connected to the actuator for closing the at least one staple,
   wherein the retractable housing is capable of being retracted proximally along the longitudinal axis over the exterior surface of the flexible shaft to expose the staple holding member and wherein said staple closer and said staple holding member are operatively connected to the actuator so as to close and release a staple.

17. The system of claim 16, wherein the staple further comprises a filament.

18. The system of claim 16, wherein the retractable housing is cylindrical or substantially cylindrical.

19. A flexible shaft stapling device comprising:
   a generally elongated flexible shaft having a longitudinal axis, proximal and distal ends, and an exterior surface;
   an actuator located at the proximal end of said flexible shaft;
   a retractable housing having proximal and distal ends and being slidably located at and at least partially surrounding the distal end of the flexible shaft;
   a staple holding member within the retractable housing at the distal end of said flexible shaft, said staple holding member being adapted for releasably holding at least one staple; and
   a stapler closer within the retractable housing and operatively connected to the actuator for closing a staple,
   wherein the retractable housing is capable of being retracted proximally along the longitudinal axis over the exterior surface of the flexible shaft to expose the staple holding member and wherein said staple closer and said staple holding member are operatively connected to the actuator so as to close and release a staple.

20. The device of claim 19, wherein the retractable housing is cylindrical or substantially cylindrical.

* * * * *